United States Patent [19]

Konno et al.

[11] Patent Number: 4,858,618
[45] Date of Patent: Aug. 22, 1989

[54] THERMODILUTION METHOD AND APPARATUS FOR DETERMINING RIGHT VENTRICULAR EJECTION FRACTION

[75] Inventors: Mark A. Konno, Costa Mesa; John A. Ripley, Newport Beach, both of Calif.

[73] Assignee: Baxter Travenol Laboratories, Inc., Deerfield, Ill.

[21] Appl. No.: 866,772

[22] Filed: May 23, 1986

[51] Int. Cl.$^4$ ............................................. A61B 5/02
[52] U.S. Cl. .................................... 128/7.3; 128/702
[58] Field of Search ............................. 128/691–694, 128/713, 702

[56] References Cited

U.S. PATENT DOCUMENTS

| 3,678,922 | 7/1972 | Phillips et al. | |
| 4,004,576 | 1/1977 | Gahuiler et al. | 128/713 |
| 4,015,593 | 4/1977 | Elings et al. | 128/713 |
| 4,023,564 | 5/1977 | Valiguette et al. | 128/708 |
| 4,326,539 | 4/1982 | Obermajer | 128/713 |
| 4,417,588 | 11/1983 | Houghton et al. | |
| 4,418,700 | 12/1983 | Warner | |
| 4,502,488 | 3/1985 | Degironimo et al. | |
| 4,632,125 | 12/1986 | Webler et al. | 128/692 |

FOREIGN PATENT DOCUMENTS 2304173 8/1974 Fed. Rep. of Germany .

OTHER PUBLICATIONS

International Conference on Biomedical Transducers, Paris, 3rd–7th Nov. 1975, Biocapt 1975, vol. 2, pp. 45–51.

N. Ohshima et al.: "A Simple Method for Measuring Cardiac Ejection Fraction".

Med. Progr. Technol., vol. 3, No. 4, Apr. 1976, pp. 161–167, Springer Verlag, Berlin, DE; A. Saadjian et al.,: "Cardiac Output Measurement by Thermodilution—Methodologic Problems".

Medical and Biological Engineering, vol. 6, No. 4, Aug. 1968, pp. 399–402, Pergamon Press, Stevenage, GB; B. W. Watson et al.; "Left Ventricular Volume Estimation in Man Using a Thermocouple in the Ascending Aorta".

Dhupar et al., A Microprocessor-Based Venticular Function Analyzer; Conference IEEE 1979 Frontiers of Engineering in Health Care Conference; pp. 145–149.

Jarlov, A. et al., Ventricular Volumes Determined from Indicator Dilution Curves; Medical & Biological Engineering & Computing; Jan. 1979 Issue; pp. 31–37.

Grune & Stratton; Progess in Cardiovascular Diseases; pp. 409–434; Mar./Apr. 1983.

Blesser, W. B.; A Systems Approach to Biomedicine; McGraw-Hill Book Co., New York 1969.

Daskalov, I. K.; Hybrid Computer for Dye-Dilution Curves; Medical & Biological Engineering & Computing; 1978; pp. 68–72.

Kay, H. R. et al.; Measurement of Ejection Fraction by (List continued on next page.)

Primary Examiner—Francis Jaworski
Assistant Examiner—John C. Hanley
Attorney, Agent, or Firm—Gordon L. Peterson

[57] ABSTRACT

A method and apparatus for determining right heart ejection fraction by injecting a cold indicator into the right ventricle or locations in the heart upstream thereof during an injection period and allowing the indicator to be diluted with blood and flow to the pulmonary artery whereby the temperature of the fluid in the pulmonary artery falls and then rises, measuring the temperature of the fluid in the pulmonary artery at least during the time that the temperature in the pulmonary artery is rising, measuring a prebolus temperature of the blood in the pulmonary artery prior to the time that the cold indicator reaches the pulmonary artery, establishing a post bolus baseline temperature which is lower than said prebolus baseline temperature, comparing at least some of the measured temperatures during the time that the temperatures of the fluid in the pulmonary artery are rising to the post bolus baseline temperature to establish temperature differentials, and using at least some of the temperature differentials to determine ejection fraction.

21 Claims, 5 Drawing Sheets

OTHER PUBLICATIONS

Thermal Dilution Techniques; Journal of Surgical Research; vol. 34; pp. 337–246.

Martyn, J. A. J. et al.; Thermodilution Right Ventricular, The Journal of Trauma; vol. 21, No. 8; pp. 619–626.

Maruschak, G. F.; Temperature Wave Distortion by Catheter-Mounted Fast Response Thermistors; Abstract.

Maruschak, G. G.; Ejection Fraction by Thermodilution (Abstract); ASA; vol. 55; No. 3; Sep. 1981.

Morrison, D. et al.; The Effect of Pulmonary Hypertension of Systolic Function of the Right Ventricle; Chest; vol. 84; No. 3; Sep. 1983, pp. 250–257.

Rapaport, E.; Usefulness and Limitations of Thermal Washout Techniques in Ventricular Volume Measurement; American Journal of Cardiology; vol. 18; Aug. 1966; pp. 226–234.

THERMODILUTION METHOD AND APPARATUS FOR DETERMINING RIGHT VENTRICULAR EJECTION FRACTION

BACKGROUND OF THE INVENTION

The right ventricle receives blood from the right atrium through the tricuspid valve and pumps the blood through the pulmonic valve to the pulmonary artery. In pumping blood, the right ventricle expands during diastole to take in blood through the tricuspid valve and contracts during systole to discharge blood through the pulmonic valve into the pulmonary artery.

It is sometimes necessary or desirable to determine the effectiveness of the right ventricle in pumping blood to the pulmonary artery, and for this purpose, right heart ejection fraction is determined. Ejection fraction is determined by comparing the expanded volume or end diastolic volume (EDV) of the right ventricle with the contracted volume or end systolic volume (ESV) of the right ventricle. Mathematically, ejection fraction (EF) can be expressed as follows:

$$EF = \frac{EDV - ESV}{EDV} \quad \text{Equation 1}$$

Ejection fraction is calculated from thermodilution curves by hand computation. Thermodilution is typically carried out by injecting a cold indicator into the right ventricle or right atrium and allowing the indicator to be diluted with blood. As this cold mixture is pumped through the right ventricle into the pulmonary artery, the temperature of the fluid in the pulmonary artery falls and then rises. The temperatures of the fluid in the pulmonary artery are measured during the time that the temperature is rising and compared with a prebolus baseline temperature of blood in the pulmonary artery to establish temperature differentials. The temperature differentials are then used to determine ejection fraction. Ejection fraction calculation is widely discussed in the literature, such as 1. *Journal of Surgical Research*, "Measurement of Ejection Fraction by Thermal Dilution Techniques", H. R. Kay et al, Vol. 34, 337–346 (1983).
2. *The Journal of Trauma*, "Thermodilution Right Ventricular Volume: A Novel and Better Predictor of Volume Replacement in Acute Thermal Injury", J. A. J. Martyn et al, Vol. 21, No. 8, 619–626 (1981).
3. *ASA*, "Ejection Fraction By Thermodilution" (Abstract), G. G. Maruschak et al, Vol. 55, No. 3, September 1981.

Hand calculation of ejection fraction is typically performed using the plateau method which can be mathematically stated as follows:

$$EF = 1 - \frac{T_{i+1} - T_B}{T_i - T_B} \quad \text{Equation 2}$$

where, $T_i$ is the temperature at any of the plateaus on the downslope (i.e. during the time the temperature in the pulmonary artery is rising) of the thermodilution curve, $T_{i+1}$ is the temperature at the immediately following plateau, and $T_B$ is the baseline temperature. Hand calculation of ejection fraction using the plateau method is, of course, slow and, as shown by equation 2, utilizes only two points in the cardiac cycle, see *American Journal of Cardiology*, "Usefulness and Limitations of Thermal Washout Techniques in Ventricular Volume Measurement", E. Rapaport, Vol. 18, 226–234, August 1966.

In addition, calculation of ejection fraction using the plateau method is consistently lower than ejection fraction as calculated using radionuclear techniques. Accordingly, it is desirable to refine the ejection fraction determinations so that more accurate results are obtained.

SUMMARY OF THE INVENTION

This invention automates EF determinations and provides other important advantages. This invention is based, in part, upon the recognition that some of the assumptions underlying the calculation of ejection fraction using equation 2 are erroneous. For example, one such assumption is that the baseline temperature $T_B$ of the blood entering the right ventricle does not change from a time just before injection of the bolus through the times that the temperature is measured in the pulmonary artery for the purpose of determining EF. This is not true if atrial injection is utilized. Because injection of the cold indicator is carried out over several heart beats, some indicator is pooled in the atrium, and this changes the baseline temperature $T_B$ of the blood entering the right ventricle from the prebolus baseline temperature prior to injection. This is one reason why ejection fraction calculations made by the plateau method tend to be low.

This invention compensates for the baseline temperature drift without adding another temperature sensor to the catheter used in taking the temperature measurements. This is accomplished by establishing a temperature versus time relationship or curve using at least some of the measured temperatures in the pulmonary artery when the temperature of fluid in the pulmonary artery is rising. This curve projects temperatures between the measured temperatures and beyond the highest measured temperature used to establish the curve. A temperature established by the curve which is below the last measured temperature is then used to establish the post bolus baseline temperature.

For the best results, the curve preferably is or approximates a first order exponential curve. This curve can be used in various different ways to approximate a post bolus baseline temperature $T_{B2}$ which produces more accurate results than the prebolus baseline temperature which is the blood temperature entering the right ventricle prior to injection of the cold indicator into the atrium. In any event, the post bolus baseline temperature will be lower than the prebolus baseline temperature due to the various cooling factors identified above.

A preferred technique for establishing the post bolus baseline temperature is to use as the post bolus baseline temperature, the temperature identified by the first order exponential curve as the curve approaches its asymptote. Although the use of this curve to establish a post bolus baseline temperature is particularly adapted for injection of the indicator upstream of the right ventricle, such as in the atrium, it may also be used for ventricular injection.

The plateau method as determined by equation 2 also assumes that the temperatures sensed in the pulmonary artery accurately represent the temperature of the fluid in the pulmonary artery. However, testing has shown that the response time of the catheter mounted temperature sensor is not adequate to monitor 100 percent of the temperature change within a given heartbeat interval. Numerical modeling provides a means by which the response time can be compensated for when the heartbeat or R—R interval is known. This enables more accurate computer measurement of the temperature changes in the pulmonary artery.

This can be accomplished, for example, by determining the response time for a group of the catheter-mounted sensors which are to be utilized. A correction factor can then be applied to the calculated EF.

Another assumption underlying the use of equation 2 is that there is no arrhythmic heart activity during the time that the temperatures in the pulmonary artery are being measured to determine ejection fraction. This invention recognizes the possibility of such arrhythmic heart activity and provides for arrhythmia detection. If arrhythmic heart activity is detected during the time of interest, an alarm is activated to advise of the arrhythmic heart activity.

The invention, together with additional features and advantages thereof, may best be understood by reference to the following description taken in connection with the accompanying illustrative drawing.

DESCRIPTION OF THE PREFERRED EMBODIMENT

Figure 1:
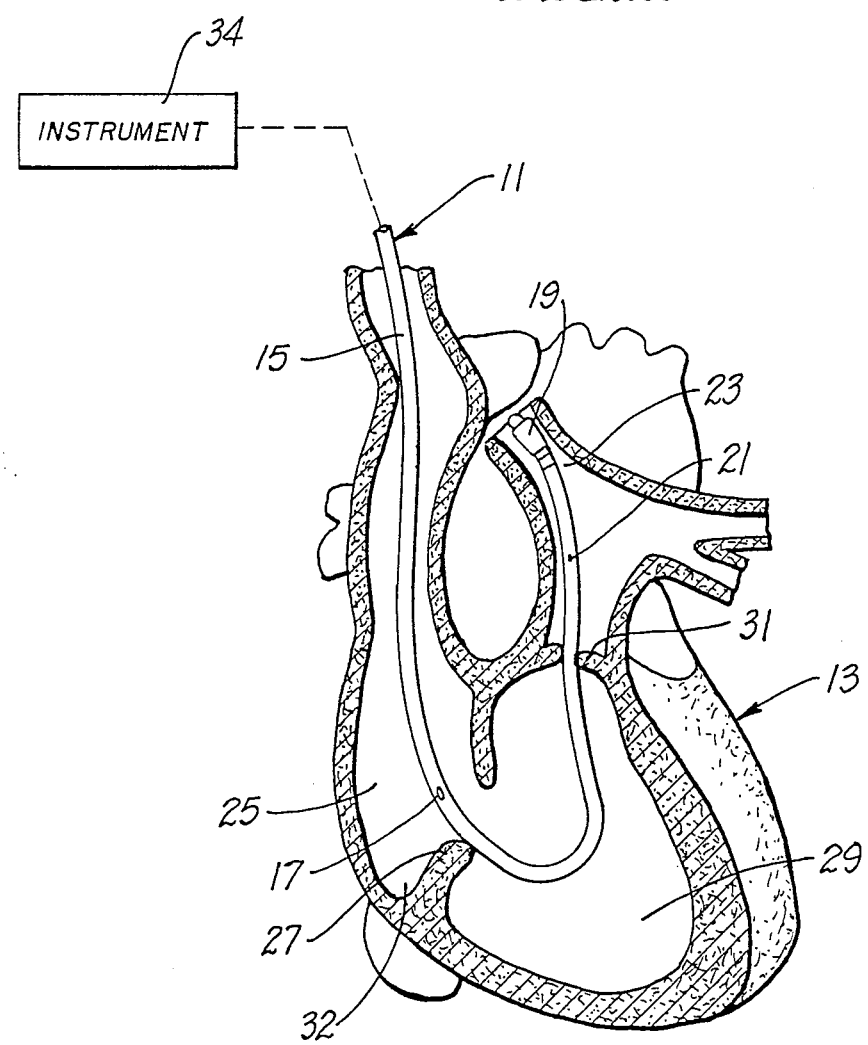
FIG. 1 is a sectional view through the right heart showing one form of catheter which can be used in the determination of ejection fraction.

FIG. 1 illustrates one form of catheter 11 inserted into a human heart 13 for the purpose of carrying out the present invention. Although the catheter 11 may be of various different constructions and be just a temperature probe, in this embodiment, the catheter includes an elongated flexible tube 15 having an injectate port 17, a balloon 19 closely adjacent the distal end of the tube and a temperature sensor in the form of a thermistor 21 proximal of the balloon but adjacent the distal end of the tube. A more complete description of the catheter 11 can be obtained from Webler et al application Ser. No. 570,631 filed Jan. 13, 1984, now U.S. Pat. No. 4,632,125, which is incorporated by reference herein.

The catheter 11 is inserted into the heart 13 using conventional medical techniques to place the balloon 19 and the thermistor 21 in pulmonary artery 23 and to place the injectate port 17 in right atrium 25. Thus, the catheter extends through tricuspid valve 27, right ventricle 29 and the pulmonic valve 31 to the pulmonary artery 23.

Figure 2:
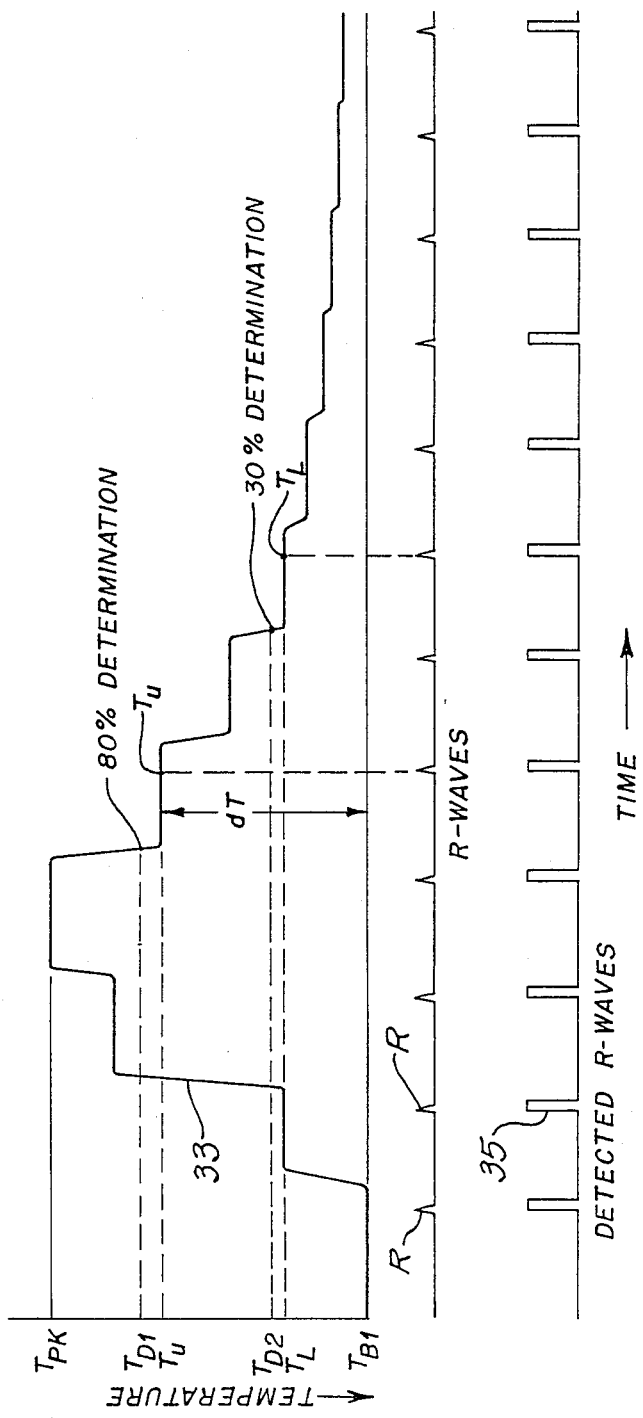
FIG. 2 is an idealized, illustrative plot of temperature of the fluid in the pulmonary artery versus time and of the corresponding "R" waves and detected "R" waves.

To determine right heart ejection fraction or cardiac output, a bolus of cold indicator, such as saline solution, is rapidly injected over several heart beats through a lumen of the tube 15 and the injectate port 17 into the right atrium 25. In the illustrated embodiment, the injectate is directed generally toward inferior vena cava 32 counter current to the blood flow from the inferior vena cava so as to provide good mixing with the blood. During diastole, the right ventricle 29 expands, and the tricuspid valve 27 opens to allow some of the blood-indicator mixture to enter the right ventricle. During systole, the right ventricle 29 contracts to force or pump the blood-indicator mixture through the pulmonic valve 31, into the pulmonary artery 23 and across the thermistor 21. Because the injection of the cold indicator takes place over multiple heart beats, the temperature of the fluid in the pulmonary artery 23 reduces from a prebolus baseline temperature $T_{B1}$ (FIG. 2) in multiple increments to a lowermost temperature or temperature peak $T_{PK}$ and then increases in increments such that the temperature curve asymptotically approaches the prebolus baseline temperature $T_{B1}$. As shown in FIG. 2, each temperature step or plateau of the thermodilution (TD) curve 33 immediately follows an "R" wave or right ventricle 29 contraction or heart beat. It should be noted that the TD curve 33 is inverted in that the prebolus baseline temperature $T_{B1}$ is a higher temperature than the temperature peak $T_{PK}$. Using the TD curve 33 and equation 2, it is possible to calculate ejection fraction as more fully described in, for example, Webler et al application Ser. No. 570,631 now U.S. Pat. No. 4,632,125 referred to above.

The present invention provides for the automated determination of ejection fraction, although hand computation utilizing the principles of this invention is also possible. This invention can be implemented with the catheter 11 and a suitable instrument 34 (FIG. 1) which may include suitable electronic hardware, software and a microcomputer or a combination of the two. A software implementation is preferred to carry out the steps shown in FIG. 3, and in that connection, it is only necessary to make certain modifications to a program known as COM-1 used by equipment available from American Edwards Laboratories of Santa Ana, Calif., for the purpose of computing cardiac output.

Figure 3:
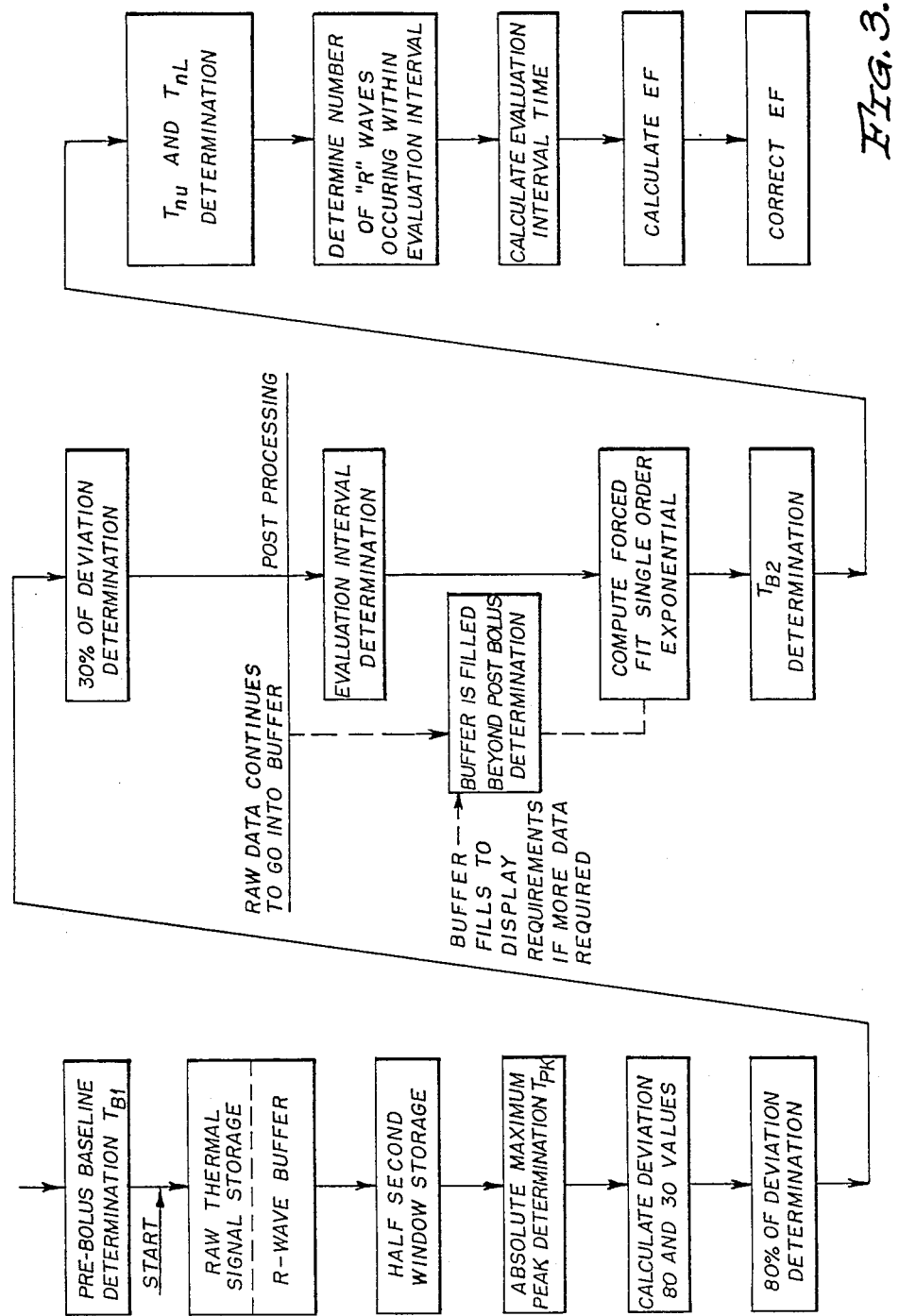
FIG. 3 is a flow chart showing the basic steps in the determination of ejection fraction.

With the catheter 11 in the heart 13 as shown in FIG. 1, the thermistor 21 provides continuous temperature information concerning the temperature of the fluid, i.e., blood or blood-indicator mixture in the pulmonary artery 21 to the instrument 34. In a digital system, this temperature information is sampled periodically, such as every 71 milliseconds by a sampler in the instrument 34. With reference to FIG. 3, and excluding the usual preliminaries of the type used in the COM-1 program, such as noisy baseline identification and thermodrift detection, the first step is prebolus baseline determination, i.e., determining the prebolus baseline temperature $T_{B1}$. To accomplish this, the temperature samples are averaged in any suitable manner, such as by calculating a running average of the samples. Although TB1 is actually measured in the pulmonary artery, it can be safely assumed that, prior to injection of the cold indicator, the temperature of the blood entering the right ventricle is the same as in the pulmonary artery.

With $T_{B1}$ determined, the operator can initiate a start command, and a bolus of cold indicator is injected through the injectate port 17 into the right atrium 25 with such injection taking place over multiple heart beats. The indicator cools the blood and forms a blood-indicator mixture which is pumped through the right ventricle 29 to the pulmonary artery to provide the TD curve 33 shown in FIG. 2. The start command also brings about the storage of raw dT values and the associated detected "R" waves 35 (FIG. 2) as, for example, a twelve-bit word. The dT values are the difference between the temperature defined by the TD curve 33 and the prebolus baseline temperature $T_{B1}$ as shown in FIG. 2. The dT samples are taken periodically, such as every 71 milliseconds, and the buffer for storing such samples may be, for example, 1024 words in length for approximately 73 seconds of storage. Every "R" wave is stored in the "R" wave buffer in the instrument 34 and is stored as a detected "R" wave 35. The "R"-wave buffer and the buffer for the dT values are synchronized in time so that, for each dT value, the presence or absence of an "R" wave during the associated dT sample time is stored as a "1" or "0" in the "R"-wave buffer. This buffer synchronization facilitates correlation between heart electrical activity and fluid movement by the heart as manifested in temperature changes, i.e., dT values. Although the dT values can be manipulated in various different ways, it is preferred to store all of the dT values. In addition, a real time running average of recent dT values is maintained, as represented by the half-second window storage. For example, every 7 dT samples may be averaged and stored as a 0.5 second average. Thus, the first 7 dT values are averaged, then dT values 2 through 8 are averaged and so on.

Next, the peak temperature $T_{PK}$, or lowest temperature, is determined. This can be accomplished, for example, by identifying the largest stored 0.5 second dT average as the peak temperature $T_{PK}$. $T_{PK}$ and the time when it occurs are stored.

Next, the deviation 80% and 30% values are calculated by multiplying 0.8 and 0.3, respectively, times the peak temperature $T_{PK}$. These calculated values are stored.

Using the stored 0.5 second dT averages, the 80 percent deviation determination is located on the TD curve 33. Specifically, the first of such average dT values following $T_{PK}$ that is equal to, or less than 0.8 times $T_{PK}$ is stored as $T_{D1}$. The time at which the temperature $T_{D1}$ occurs is also stored.

Similarly, the 30 percent of deviation determination is also located. The first of the stored average dT values following $T_{PK}$ that is equal to or less than 0.3 times the temperature $T_{PK}$ is identified as $T_{D2}$ and is stored along with its reference time.

Establishing $T_{D1}$ and $T_{D2}$ as approximately equal to 0.8 times $T_{PK}$ and 0.3 times $T_{PK}$, respectively, is desirable but not critical. However, other points on the downslope of the TD curve 33 between about 0.95 times $T_{PK}$ and 0.15 times $T_{PK}$ can be used, if desired.

The evaluation interval is then determined as the first step of post processing. To enhance repeatability and allow for a good curve fit, it is desired to consistently locate the evaluation interval in accordance with a particular program. Generally, this can be accomplished by determining the "R" waves occurring closest to $T_{D1}$ and $T_{D2}$ and their respective times of occurrence. Various programs for choosing such "R" waves can be used. For example, if $T_{D1}$ occurs between "R" waves, the first of such "R" waves, i.e., the "R" wave nearer $T_{PK}$, is used to establish the upper limit temperature $T_u$ if such "R" wave's corresponding temperature amplitude is within 12.5 percent of the temperature $T_{D1}$ and is less than 90 percent of the peak temperature $T_{PK}$. Also, this "R" wave must occur after the occurrence of the peak temperature $T_{PK}$. If these synchronization conditions are met for such first "R" wave, then the temperature corresponding to the time of occurrence of such "R" wave will be used as the upper limit temperature $T_u$. If these synchronization conditions cannot be achieved for such first "R" wave, then the temperature corresponding to the time of occurrence of the "R" wave immediately following the occurrence of the temperature $T_{D1}$ will be used as the upper limit temperature $T_u$.

The "R" wave nearest the temperature $T_{D2}$ must be at least two R—R intervals beyond the upper "R" wave. If the "R" wave which is two R—R intervals forward down the TD curve 33 is from 15 to 30 percent of $T_{PK}$, then this point is used as $T_L$ as shown in FIG. 2. If this "R" wave is above 30 percent of $T_{PK}$, then the temperature that corresponds to the "R" wave that is closest to 30 percent of $T_{PK}$ is used. If the temperature along the TD curve 33 at the end of the second R—R interval is less than 15 percent of $T_{PK}$, then the temperature at the end of the first R—R interval is used for $T_L$. If the temperature at the first R—R interval is still less than 15 percent of $T_{PK}$, an error message is given.

The respective upper and lower limit temperature values $T_u$ and $T_L$ are stored and each is preferably an average, such as a 3-point average, of the data on each side of the associated "R" wave. For example, if $T_2$ corresponds to the lower "R" wave synchronization point, the actual temperature used for $T_L$ would be as follows:

$$T_L = \frac{T_1 + T_2 + T_3}{3} \qquad \text{Equation 3}$$

where, $T_1$ and $T_3$ are stored temperatures dT on opposite sides of $T_2$.

The temperatures $T_L$ and $T_u$ which also constitute evaluation limits always coincide with "R" wave events as shown in FIG. 2.

Figure 4:
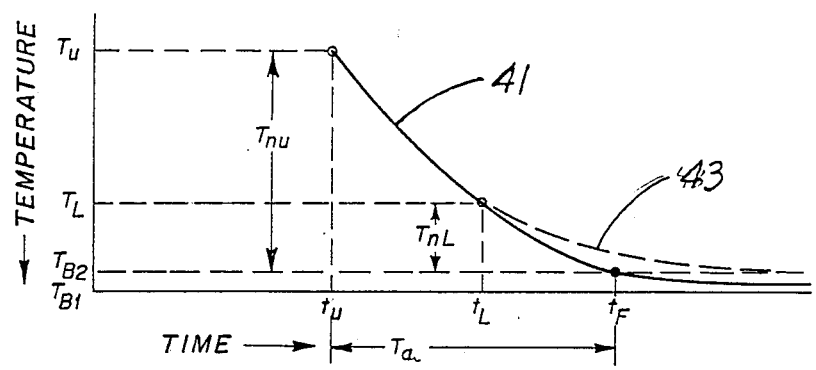
FIG. 4 is a plot of temperature versus time illustrating how the post bolus baseline temperature is established.

Next a post bolus baseline temperature $T_{B2}$ is determined utilizing $T_u$ and $T_L$ and force fitting a first order exponential curve to these two points as shown in FIG. 4. This calculation is made using the prebolus baseline temperature $T_{B1}$ as follows:

$$TD = \Delta e^{-t/\tau} \qquad \text{Equation 4}$$

where,
TD is the value on the curve 41
$\Delta$ is the temperature $T_u$
t is time and $$\tau = \frac{t_L - t_u}{\ln(T_u/T_L)}$$

where,
$t_L$ is the time at which $T_L$ occurs and
$t_u$ is the time at which $T_u$ occurs.

Thus, by implementing equation 4, the curve 41 of FIG. 4 can be plotted and extrapolated beyond $T_L$. Because the curve 41 is or approximates a first order exponential curve, it asymptotically approaches the prebolus baseline temperature $T_{B1}$.

This invention establishes as the post bolus baseline temperature $T_{B2}$ the temperature which exists near the time when the curve 41 closely approaches $T_{B1}$. Although various levels can be employed, a preferred approach is to utilize a threshold of 0.01 to 0.05 of $T_{PK}$ with 0.03 to $T_{PK}$ being optimum. The time $t_f$ at which this threshold temperature occurs can be obtained by solving for "t" in equation 4 which yields $t_a$, which is the difference between $t_F$ and $t_u$. The time $t_F$ can be found from the equation $t_F = t_u + t_a$. Next, the raw temperature data that corresponds to the time $t_F$ is located, and this is established as the post bolus baseline temperature $T_{B2}$. Preferably, an average, such as a 70-point average of the temperature data beginning at $t_F$ is used to establish the post bolus baseline $T_{B2}$, i.e., an average of the temperatures occurring in the pulmonary artery in the next 2.5 to 5 seconds may be used to establish $T_{B2}$.

The post bolus baseline temperature $T_{B2}$ is subtracted from the curve 41 to provide a new upper limit temperature $T_{nu}$ and a new lower limit temperature $T_{nL}$. A new curve 43 can then be force fit to the new upper and lower limit temperatures $T_{nu}$ and $T_{nL}$ as shown in dashed lines in FIG. 4. The curve 43 asymptotically approaches the post bolus baseline temperature $T_{B2}$. The number of "R" waves occurring during the evaluation interval, i.e., between $t_u$ and $t_L$ are determined, and the duration of the evaluation interval is calculated. From this, preliminary ejection fraction can be calculated from the following equation:

$$EF = 1 - e^{-\frac{1}{\tau} \times \frac{EIT}{n}} \quad \text{Equation 5}$$

$$\text{where, } \tau = \frac{t_L - t_u}{\ln(T_{nu}/T_{nL})}$$

$$EIT = t_L - t_u$$

n = the number of "R" waves occurring during the evaluation interval.

The preliminary ejection fraction calculation is then corrected based upon the response time of the catheter mounted thermistor 21. For this purpose, the response of the catheter mounted thermistor 21 is plotted as a function of time using any suitable technique, and one such plot for the thermistor 21 as mounted on the catheter 11 is shown in FIG. 5.

Figure 5:
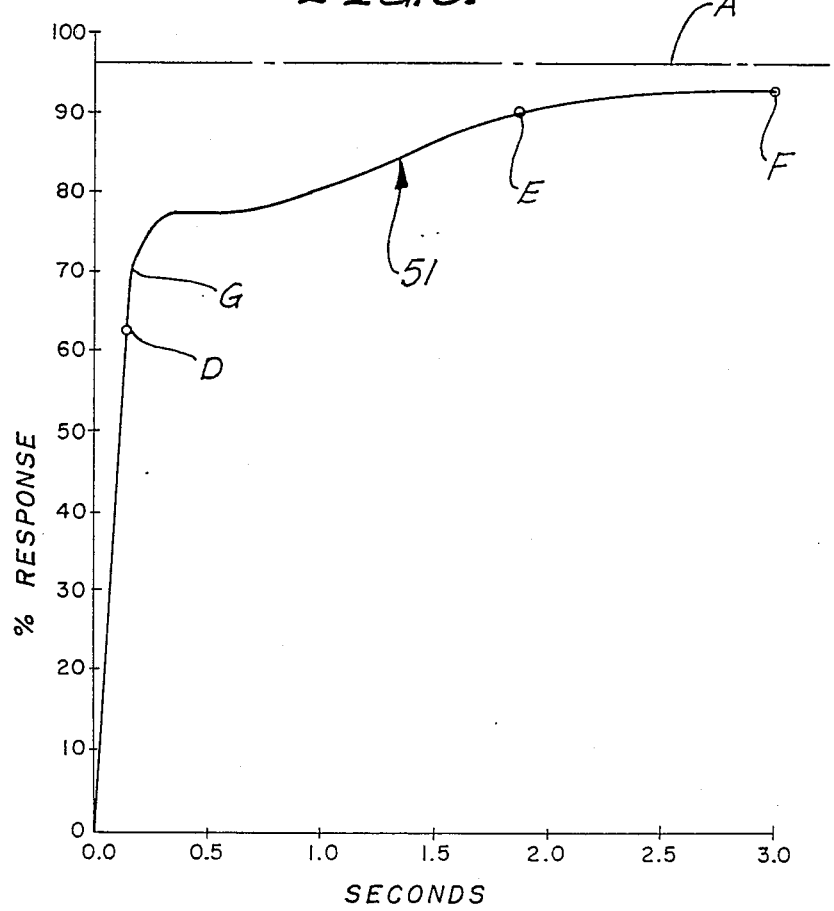
FIG. 5 is a plot of percent response versus time for one catheter-mounted thermistor that may be used in carrying out this invention.

Although various techniques can be utilized to determine the response, to plot FIG. 5, a group of the catheters 11 having the thermistor 21 thereon were tested for response time data at the 63 percent, 90 percent and 95 percent responses. The average of these data points at these responses are shown by the points D, E, F on the response curve 51. Beyond the point F, the curve 51 approaches an asymptote A which represents the maximum percent response for the catheter-mounted thermistor. For a catheter mounted thermistor, a second order exponential curve 51 is a good approximation of the percent response as a function of time, with the curve 51 being influenced primarily by the first order component from the origin to a division response or point G, which, in this example, is beyond the point D and at about 70 percent response, and with the curve 51 being primarily influenced by the second order component above, response G. By placing a time delay before the second order component, its effect on the first order component is delayed; hence the shape of the curve between the points G and E. The functional form of the equation for the second order exponential curve 51 is:

$$A[1 - e^{(-Bt)} - (t)e^{(-Ct)}] = \% \text{ response} \quad \text{Equation 6}$$

where,
A is the % response at the asymptote,

B and C are the first and second order slope coefficients, and t is time.

The best curve fit using this form is achieved with A equal to 97, B equal to 12 and C equal to 1.8.

As shown by FIG. 2, the temperature during the downslope of the curve 33 changes with each heart beat. Accordingly, the time for the thermistor 21 to react to a temperature change is equal to the R—R interval. The model shown by way of example in FIG. 5 shows the known approximate percent response to temperature change as a function of time, i.e., about how rapidly the catheter-mounted thermistor 21 responds during any given time interval. Although this could be used to correct every temperature value, this would be quite complex, and it has been found that a good approximation for correcting the ejection fraction can be determined as follows:

$$EF = \text{Preliminary } EF \times \frac{100\%}{\% \text{ response}} \quad \text{Equation 7}$$

To utilize equation 7, the length of the R—R interval or the average length of such intervals between $t_u$ and $t_L$ determine the time in seconds, and from this the actual percent response can be determined from the curve 51. Thus, R—R interval of one second would provide an 80 percent actual response which in turn would provide a correction factor of 1.25 which should be multiplied by the preliminary EF to obtain the corrected ejection fraction.

Of course, the ejection fraction can be calculated multiple times from multiple injections of cold indicator, if desired. The mathematical functions and the steps described above can be readily implemented with software.

An optional, but important, feature of the invention is the setting of a flag or the providing of an alarm if any arrhythmic heart activity occurs during the evaluation interval. This can be accomplished by appropriate monitoring of the "R" wave data stored in the "R" wave buffer. Although this can be accomplished in different ways, the present invention provides a 4-beat running average of the "R" wave intervals with all abnormal beats and the beat following any abnormal beat not being used in the average; i.e., with each new beat, a new average of the 4 most recent normal beats is taken. Although various factors could be monitored, this invention considers heart activity which is out of range, premature, or delayed to be abnormal or arrhythmic in nature. For example, individual heart beats and the preceeding R—R interval which are equivalent to heart rates below 35 per minute or over 180 per minute are considered out of range. Delayed beats are those which are separated by more than one-and-one-half times the current 4-beat average, and a premature beat is any beat which has its preceding R—R interval 20 beats per minute faster than the current 4-beat average. Thus, the present invention provides an alarm if any out of range, delayed or premature beats occur during the evaluation interval by monitoring the stored R-wave data.

Figure 6:
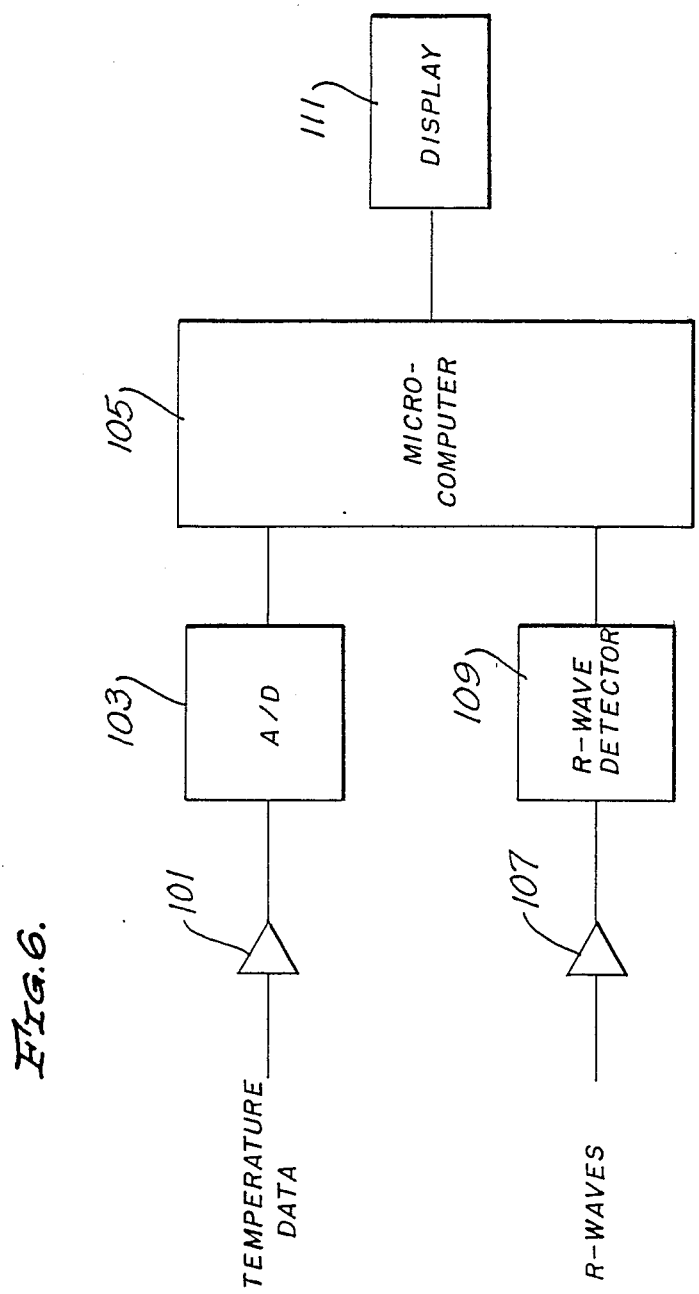
FIG. 6 is a block diagram showing one apparatus embodying the invention.

FIG. 6 shows by way of example a block diagram of the components of the instrument 34. Analog temperature data from the catheter 11 is fed through an isolation amplifier 101 to an A/D converter which samples the raw temperature data periodically, such as every 71 milliseconds, to provide dT temperature samples or values to a microcomputer 105. Similarly, "R"-wave information is fed through an isolation amplifier 107 to an "R"-wave detector 109 which provides the detected "R" waves 35 to the microcomputer 105. The microcomputer 105 has the storage capability to store the temperature samples dT and the detected "R" waves 35 and to perform the other functions discussed above. A display 111 may be provided to display, for example, the calculated ejection fraction.

As used herein, the term "catheter" refers to any probe or catheter. The injection and temperature-measuring functions of the catheter can be carried out by separate catheters, if desired.

Although an exemplary embodiment of the invention has been shown and described, many changes, modifications and substitutions may be made by one having ordinary skill in the art without necessarily departing from the spirit and scope of this invention.

We claim:

1. An apparatus for determining right heart ejection fraction comprising:
   means for injecting a cold indicator into the right ventricle or locations in the heart upstream thereof during an injection period and allowing the indicator to be diluted with blood and flow to the pulmonary artery whereby the temperature of the fluid in the pulmonary artery falls and then rises;
   means for measuring the temperature of the blood in the heart to provide a prebolus temperature of the blood prior to the time that the cold indicator reaches the pulmonary artery and to provide measured temperatures of the fluid in the pulmonary artery during the time that the temperature in the pulmonary artery is rising;
   means responsive to at least some of the measured temperatures for establishing a post bolus baseline temperature which is lower than said prebolus baseline temperature; and
   means responsive to differentials between at least some of the temperatures measured during the time that the temperature of the fluid in the pulmonary artery is rising and the post bolus baseline temperature for determining right heart ejection fraction.

2. An apparatus as defined in claim 1 wherein said measuring means includes a temperature sensor carried by a catheter having a known approximate percent response to temperature change as a function of time, and said ejection fraction determining means is further responsive to the known approximate percent response of the temperature sensor as carried by the catheter for determining ejection fraction.

3. An apparatus as defined in claim 1 including means for monitoring the heart beats of the patient and means for providing an alarm if the monitored heart beats show any arythmic heart activity during the time that the temperatures of the fluid in the pulmonary artery are rising.

4. An apparatus as defined in claim 3 wherein said measuring means includes a temperature sensor carried by a catheter having a known approximate percent response to temperature change as a function of time, and said ejection fraction determining means is further responsive to the known approximate percent response of the temperature sensor as carried by the catheter for determining ejection fraction.

5. An apparatus as defined in claim 1 wherein said post bolus baseline temperature establishing means includes means for establishing a temperature-versus-time relationship using at least some of the measured temperatures of the fluid in the pulmonary artery when the temperature of the fluid in the pulmonary artery is rising, with the relationship projecting temperatures between the measured temperatures and above the highest measured temperature used in establishing the relationship, and means responsive to a temperature established by the relationship to establish said post bolus baseline temperature.

6. A method of determining right heart ejection fraction comprising:
   injecting a cold indicator into the right ventricle or locations in the heart upstream thereof during an injection period and allowing the indicator to be diluted with blood and flow to the pulmonary artery whereby the temperature of the fluid in the pulmonary artery falls and then rises;
   measuring a prebolus temperature of the blood in the heart which has not been cooled by the cold indicator;
   measuring the temperature of the fluid in the pulmonary artery at least during the time that the temperature in the pulmonary artery is rising to provide measured temperatures;
   establishing a post bolus baseline temperature using at least some of the measured temperatures obtained when the temperature in the pulmonary artery is rising such that the post bolus temperature is lower than said prebolus baseline temperature;
   comparing at least some of the temperatures measured during the time that the temperatures of the fluid in the pulmonary artery are rising to the post bolus baseline temperature and establishing temperature differentials therebetween; and
   using at least some of the temperature differentials to determine right heart ejection fraction.

7. A method as defined in claim 6 wherein the step of measuring the temperature of the fluid is carried out with a temperature sensor carried by a catheter having a known approximate percent response to temperature change as a function of time and said step of using includes using the known approximate percent response of the temperature sensor as carried by the catheter in determining ejection fraction.

8. A method as defined in claim 6 including monitoring the heart beats of the patient and providing an alarm if the monitored heart beats show any arythmic heart activity during the time that the temperatures of the fluid in the pulmonary artery are rising.

9. A method as defined in claim 8 wherein the step of measuring the temperature of the fluid is carried out with a temperature sensor carried by a catheter having a known approximate percent response to temperature change as a function of time and said step of using includes using the known approximate percent response of the temperature sensor as carried by the catheter in determining ejection fraction.

10. A method as defined in claim 6 wherein said step of establishing a post-bolus-baseline temperature includes establishing a temperature-versus-time relationship using at least some of the measured temperatures of the fluid in the pulmonary artery when the temperature of the fluid in the pulmonary artery is rising, with the relationship projecting temperatures between the measured temperatures and above the highest measured temperature used in establishing the relationship, and using the relationship to establish said post bolus baseline temperature.

11. A method as defined in claim 10 wherein said relationship at least approximates a first order exponential curve.

12. A method as defined in claim 6 wherein the step of establishing a post bolus baseline temperature includes determining a peak temperature differential which is the difference between substantially the lowest temperature of fluid in the pulmonary artery resulting from said step of injecting and the prebolus baseline temperature, using said peak temperature differential to establish said temperature-versus-time relationship, and using a temperature which exists in said relationship which corresponds to about 1 percent to about 5 percent of the peak temperature as the post bolus baseline temperature.

13. A method as defined in claim 6 wherein said step of establishing includes force fitting a first order exponential curve to two averages of selected ones of said measured temperatures and said prebolus baseline temperature and using said curve in establishing said post bolus baseline temperature.

14. An apparatus for determining right heart ejection fraction comprising:
means for injecting a cold indicator into the right ventricle or locations in the heart upstream thereof during an injection period and allowing the indicator to be diluted with blood and flow to the pulmonary artery whereby the temperature of the fluid in the pulmonary artery falls and then rises;
a catheter adapted to be inserted into the heart and a temperature sensor carried by said catheter and adapted to be positioned in the pulmonary artery, said temperature sensor as carried by said catheter having a known approximate percent response to temperature change as a function of time, said temperature sensor being capable of measuring the temperature of the fluid in the pulmonary artery; means for monitoring heartbeat intervals; means responsive to a monitored heartbeat interval and the known approximate percent response to temperature change as a function of time of said temperature sensor as carried by said catheter for determining an actual percent response of said temperature sensor for said heartbeat interval and
means responsive to at least some of the measured temperatures during the time that the temperature of the fluid in the pulmonary artery is rising and to the actual percent response of the temperature sensor as carried by the catheter for determining right heart ejection fraction.

15. An apparatus as defined in claim 14 wherein said ejection fraction determining means includes means for determining preliminary ejection fraction (Preliminary EF) using assumed 100 percent response of the temperature sensor and means for determining corrected ejection fraction (EF) as $$EF = \text{Preliminary } EF \times \frac{100\%}{\% \text{ response}}$$

where % response is said actual precent response.

16. An apparatus as defined in claim 14 further including means for monitoring the heart beats of the heart and means for providing an alarm if the monitored heart beats show any arythmic heart activity during the time that the temperature of the fluid in the pulmonary artery is rising.

17. An apparatus as defined in claim 14 wherein the known approximate percent response of the temperature sensor as carried by the catheter varies with time and defines a second order exponential curve with the first order component primarily influencing the curve up to a division response and the second order component primarily influencing the curve above the division response.

18. A method of determining right heart ejection fraction comprising:
injecting a cold indicator into the right ventricle or locations in the heart upstream thereof during an injection period and allowing the indicator to be diluted with blood and flow to the pulmonary artery whereby the temperature of the fluid in the pulmonary artery falls and then rises;
measuring the temperature of the fluid in the pulmonary artery at least during the time that the temperature in the pulmonary artery is rising using a temperature sensor carried by a catheter with the temperature sensor as carried by the catheter having a known approximate percent response to temperature change as a function of time;
comparing at least some of the temperatures measured during the time that the temperatures of the fluid in the pulmonary artery are rising to a baseline temperature to establish temperature differentials;
monitoring the heartbeat intervals during said step of measuring;
using a monitored heartbeat interval and the known approximate percent response to temperature change as a function of time of said temperature sensor as carried by said catheter to determine an actual percent response for said heartbeat interval; and
using at least some of the temperature differentials and said actual response of the temperature sensor as carried by the catheter to determine right heart ejection fraction.

19. A method as defined in claim 18 wherein said step of using includes determining preliminary ejection fraction (Preliminary EF) using assumed 100 percent response of the temperature sensor and determining corrected ejection fraction (EF) as $$EF = \text{Preliminary } EF \times \frac{100\%}{\% \text{ response}}$$

where % response is said actual percent response.

20. A method as defined in claim 18 further including monitoring the heart beats of the patient and providing an alarm if the monitored heart beats show any arythmic heart activity during the time that the temperature of the fluid in the pulmonary artery is rising.

21. A method as defined in claim 18 wherein the known approximate percent response of the temperature sensor as carried by the catheter varies with time in accordance with $$A[1-e^{(-Bt)}\cdot(t)e^{(-Ct)}] = \% \text{ response}$$

where,
A is the percent response at an asymptote,
B and C are the first and second order slope coefficients, and
t is time.

* * * * *

UNITED STATES PATENT AND TRADEMARK OFFICE
CERTIFICATE OF CORRECTION

PATENT NO. : 4,858,618

DATED : August 22, 1989

INVENTOR(S) : Mark A. Konno et al

It is certified that error appears in the above-identified patent and that said Letters Patent is hereby corrected as shown below:

Column 6, line 67 change ".03 to" to -- .03 of --.

Column 8, line 28 after "Thus," insert -- an --.

Column 11, line 61 change "precent" to -- percent --.

Signed and Sealed this

Twenty-eighth Day of August, 1990

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,858,618
DATED : August 22, 1989
INVENTOR(S) : Mark A. Konno et al It is certified that error appears in the above-identified patent and that said Letters Patent is hereby corrected as shown below:

Column 6, line 67 change ".03 to" to -- .03 of --.

Column 8, line 28 after "Thus," insert -- an --.

Column 11, line 61 change "precent" to -- percent --.

Column 12, line 37 after "said actual" insert -- percent --.

This certificate supersedes Certificate of Correction issued August 28, 1990.

Signed and Sealed this

Thirteenth Day of November, 1990

Attest:

HARRY F. MANBECK, JR.

*Attesting Officer*     *Commissioner of Patents and Trademarks*